(12) United States Patent
Faul

(10) Patent No.: US 7,200,443 B2
(45) Date of Patent: Apr. 3, 2007

(54) TRANSCUTANEOUS ELECTRICAL NERVE STIMULATOR FOR APPETITE CONTROL

(76) Inventor: John Faul, Room H3149, Division of PCCM, Sumc, CA (US) 94305-5236

( * ) Notice: Subject to any disclaimer, the term of this patent is extended or adjusted under 35 U.S.C. 154(b) by 395 days.

(21) Appl. No.: 10/680,587

(22) Filed: Oct. 7, 2003

(65) Prior Publication Data

US 2005/0075678 A1 Apr. 7, 2005

(51) Int. Cl.
*A61N 1/18* (2006.01)

(52) U.S. Cl. .............................. 607/40; 607/45; 607/58

(58) Field of Classification Search ............ 607/39–41, 607/43, 45–46, 58
See application file for complete search history.

(56) References Cited

U.S. PATENT DOCUMENTS

| | | | |
|---|---|---|---|
| 3,411,507 A | 11/1968 | Wingrove | |
| 4,646,744 A | 3/1987 | Capel | |
| 5,067,495 A * | 11/1991 | Brehm | 607/46 |
| 5,188,104 A | 2/1993 | Wernicke et al. | |
| 5,423,872 A | 6/1995 | Cigaina | |
| 5,514,175 A * | 5/1996 | Kim et al. | 607/136 |
| 5,690,691 A | 11/1997 | Chen et al. | |
| 6,104,955 A | 8/2000 | Bourgeois | |
| 6,129,685 A | 10/2000 | Howard, III | |
| 6,564,101 B1 | 5/2003 | Zikria | |
| 6,571,127 B1 | 5/2003 | Ben-Haim et al. | |
| 6,587,719 B1 | 7/2003 | Barrett et al. | |
| 6,600,953 B2 | 7/2003 | Flesler et al. | |
| 6,775,573 B2 * | 8/2004 | Schuler et al. | 607/40 |
| 2003/0181959 A1 * | 9/2003 | Dobak, III | 607/58 |

OTHER PUBLICATIONS

"Stimulation of auricular acupuncture points in weight loss," Richards et al., Aust. Fam. Physician, Jul. 1998, 27 Suppl 2:S73-77.*

"Study on the effect of transcutaneous electric nerve stimulation on obesity" Tian et al., Beijing Da Xue Xue Bao, Jun. 18, 2003; 35 (3) 277-9 (Abstract provided in English).*

"The Effect of Transcutaneous Nerve Stimulation (TENS) on Gastric Electrical Activity," Furgala et al., Journal of Physiology and Pharmacology 2001, 52, 4, 603-610.).*

Lin, et al., Hardware—software co-design of portable functional gastrointestinal stimulator system, Journal of Medical Engineering & Technology, vol. 27, No. 4 (Jul./Aug. 2003), pp. 164-177.

* cited by examiner

*Primary Examiner*—George Manuel
*Assistant Examiner*—Nicole Kramer
(74) *Attorney, Agent, or Firm*—Vierra Magen Marcus & DeNiro LLP

(57) ABSTRACT

A method for the treatment of eating and gastrointestinal disorders through transcutaneous electrical nerve stimulation of the sympathetic celiac ganglia and nerve pathways innervating the stomach.

17 Claims, 4 Drawing Sheets

TRANSCUTANEOUS ELECTRICAL NERVE STIMULATOR FOR APPETITE CONTROL

BACKGROUND OF THE INVENTION

1. Field of the Invention

The present invention relates to the treatment of eating and gastrointestinal disorders, and in particular to the treatment of eating and gastrointestinal disorders through transcutaneous electrical nerve stimulation ("TENS") of the sympathetic nerve pathways innervating the stomach.

2. Description of the Related Art

According to the American Medical Association, obesity is reaching epidemic proportions, affecting over 30% of American adults, or almost 70 million people. And that percentage is climbing. In addition to the health risks presented by obesity itself, obesity increases the likelihood of a wide range of significant co-morbid health risks including cardiovascular complications (such as hypertension and hyperlipidemia), diabetes, gallbladder disease, cancer, polycystic ovary disease, pregnancy-related problems, arthritis-related problems and other orthopedic complications caused by stress on body joints.

Obesity may have several causes. Genetic, environmental and psychological factors are all believed to play a role in obesity. The mechanism for weight gain includes impaired metabolism of adipose tissue, physical inactivity (due to lifestyle or other illness), and uncontrolled appetite. Some illnesses, such as hypothyroidism, Cushing's disease and depression can also lead to obesity partly through hormonal effects, and partly through changes in appetite and lifestyle.

Regarding hormonal effects on obesity, the control of thyroid hormone secretion and adrenal gland secretion is at the level of the hypothalamus and pituitary regions of the brain. The hypothalamus secretes thyroid releasing factor which leads to release of thyroid stimulation hormone from the pituitary gland leading to increases in thyroid hormone production and release from the thyroid gland. In a similar fashion Corticotrophin releasing factor released from the hypothalamus leads to release of adrenocorticotrophic hormone that causes increased cortisol secretion from the adrenal glands causing Cushing's disease.

Obesity may further be caused by certain drugs, such as steroids and some antidepressants and these effects are also thought to occur in the appetite centers in the brain. Obesity is a common feature of neurologic diseases that appear to affect the appetite control center in the hypothalamic, pituitary, and brain stem regions of the brain. Kline-Levine syndrome, sarcoidosis of the hypothalamus, tumors of the hypothalamus, for example, are associated with massive obesity.

When diet therapy proves ineffective, morbid obesity is often treated through bariatric surgery. A pair of common bariatric surgical procedures are adjustable gastric banding and vertical banded gastroplasty (VBG). In these procedures, a band is surgically placed around the upper part of the stomach creating a small pouch. The pouch fills quickly when eating or drinking giving the patient the sensation of satiety. Another popular treatment is the Roux-en-Y gastric bypass, in which a small stomach pouch is created, and a section of the small intestine is attached to the pouch to allow food to bypass the lower stomach, the duodenum, and the first portion of the jejunum. This bypass reduces the amount of calories and nutrients the body absorbs. It is also known to surgically place a balloon within the stomach which then may be inflated with saline to induce a feeling of satiety. A still further surgical treatment for obesity is a gastric pacemaker, which is surgically implanted into the wall of the stomach. Electrical impulses from the device stimulate nerves to reduce appetite. Gastric pacemakers have also been known as a treatment for gastroparesis, a condition where peristalsis is impaired due to the slowing or stopping of the natural gastric slow wave pacemaker activity of the enteric nerve plexus innervating the stomach. Though there are many causes, gastroparesis often results from diabetes or damage to the vagus nerve(s).

Each of the above-described bariatric procedures has associated risks. A significant concern with banded surgeries is a high incidence of complications, such as bleeding and/or obstruction. Though generally better tolerated than banded procedures, the Roux-en-Y gastric bypass still results in significant complications, such as vitamin and mineral deficiencies, and may lead to osteoporosis in the long-term.

Additionally, while any surgical procedure involves risks, surgical procedures on obese patients present significantly higher risks of complications and death. The obesity itself as well as any co-morbid conditions associated with obesity makes it difficult to administer anesthesia in proper doses. The surgical wounds often do not heal properly. And obese patients face a higher risk of complications after surgery, such as deep venous thrombosis.

Severe weight loss and abnormal loss of appetite is an equally serious condition that can lead to suffering and death. The most common example is anorexia nervosa, a condition that classically affects young women and is associated with pathologic alterations of hypothalamic and pituitary gland function. Severe anorexia can also occur in bowel conditions that cause early satiety (a feeling of fullness) or pain on eating. While anorexia is treatable with behavioral modifications, most patients require psychotropic drugs that appear effective in increasing appetite.

Transcutaneous electrical nerve stimulation, or TENS, uses a small electrical device to deliver electrical impulses through the skin via electrode pads affixed to the skin. It is typically used to reduce pain, but TENS has also been used to relieve stiffness and improve mobility. TENS is thought to work by at least one of two physiological processes. The first is by the so-called gate control theory of pain. According to this theory, small diameter nerve fibers carry pain stimuli through a theoretical "gate mechanism" but larger diameter nerve fibers can inhibit the transmission of pain stimuli by the smaller nerves, in effect blocking or closing this theoretical gate. It is believed that by stimulating the large nerve fibers through TENS, the gate can be closed to block the pain. Under the second theory, TENS is believed to stimulate the production of endorphins, which are natural pain relieving hormones produced by the body.

SUMMARY OF THE INVENTION

It is an advantage of the present invention to provide a non-surgical alternative to treatment of overactive appetite disorders.

It is a further advantage of the present invention to provide a non-surgical alternative to treatment of underactive appetite disorders.

It is another advantage of the present invention to treat overactive and underactive appetite disorders using TENS.

It is a further advantage of the present invention to stimulate the nervous pathways innervating the stomach to suppress appetite and induce the feeling of satiety.

It is a still further advantage of the present invention to stimulate the nervous pathways innervating the stomach to allow control of gut motility and appetite a stimulus received extraneously by the patient.

It is another advantage of the present invention to treat gastroparesis or other abnormalities of bowel motility (including dumping syndrome, irritable bowel syndrome, spastic colon, constipation, and disorders of rapid bowel transit) using TENS.

These and other advantages are provided by the present invention which in preferred embodiments relates to the treatment of eating and gastrointestinal disorders through TENS. In one embodiment, a pair of external electrodes are applied to the skin along the spine, preferably encompassing T6 through T10 of the thoracic spine where the sympathetic celiac ganglia leave the spine for the stomach. Application of a modulated current to the area stimulates the celiac ganglia and enteric nerve plexus associated with the stomach, which in turn send signals to the brain indicating satiety and loss of appetite.

The modulated voltage may be applied periodically for different periods of time for about 30 days, and customized according to patients' needs and responses over time with respect to duration, amplitude and frequency to generate the desired change in appetite or bowel motility. Moreover, the stimulation of the nerve pathways signaling satiety and loss of appetite over time hyper-sensitizes the pathway so as to generate faster and more pronounced response to stimulus.

While a preferred embodiment of the present invention may be used to suppress appetite, it is understood that the present invention may alternatively be used to stimulate appetite or stimulate bowel motility or as a treatment for gastroparesis. In this embodiment, stimulation of the sympathetic celiac nerve fibers in accordance with the present invention may effectively stimulate enteric nerve plexus to entrain the naturally occurring nervous stimulation of the gut, including the natural gastric pacemaker.

BRIEF DESCRIPTION OF THE DRAWINGS

The present invention will now be described with reference to the drawings, in which.

DETAILED DESCRIPTION

The present invention now will be described more fully with reference to FIGS. 1 through 4, in which preferred embodiments of the invention are shown. The present invention may, however, be embodied in many different forms and should not be construed as being limited to the embodiments set forth herein; rather these embodiments are provided so that this disclosure will be thorough and complete and will fully convey the invention to those skilled in the art. Indeed, the invention is intended to cover alternatives, modifications and equivalents of these embodiments, which are included within the scope and spirit of the invention as defined by the appended claims. Furthermore, in the following detailed description of the present invention, numerous specific details are set forth in order to provide a thorough understanding of the present invention. However, it will be clear to those of ordinary skill in the art that the present invention may be practiced without such specific details.

Figure 1:
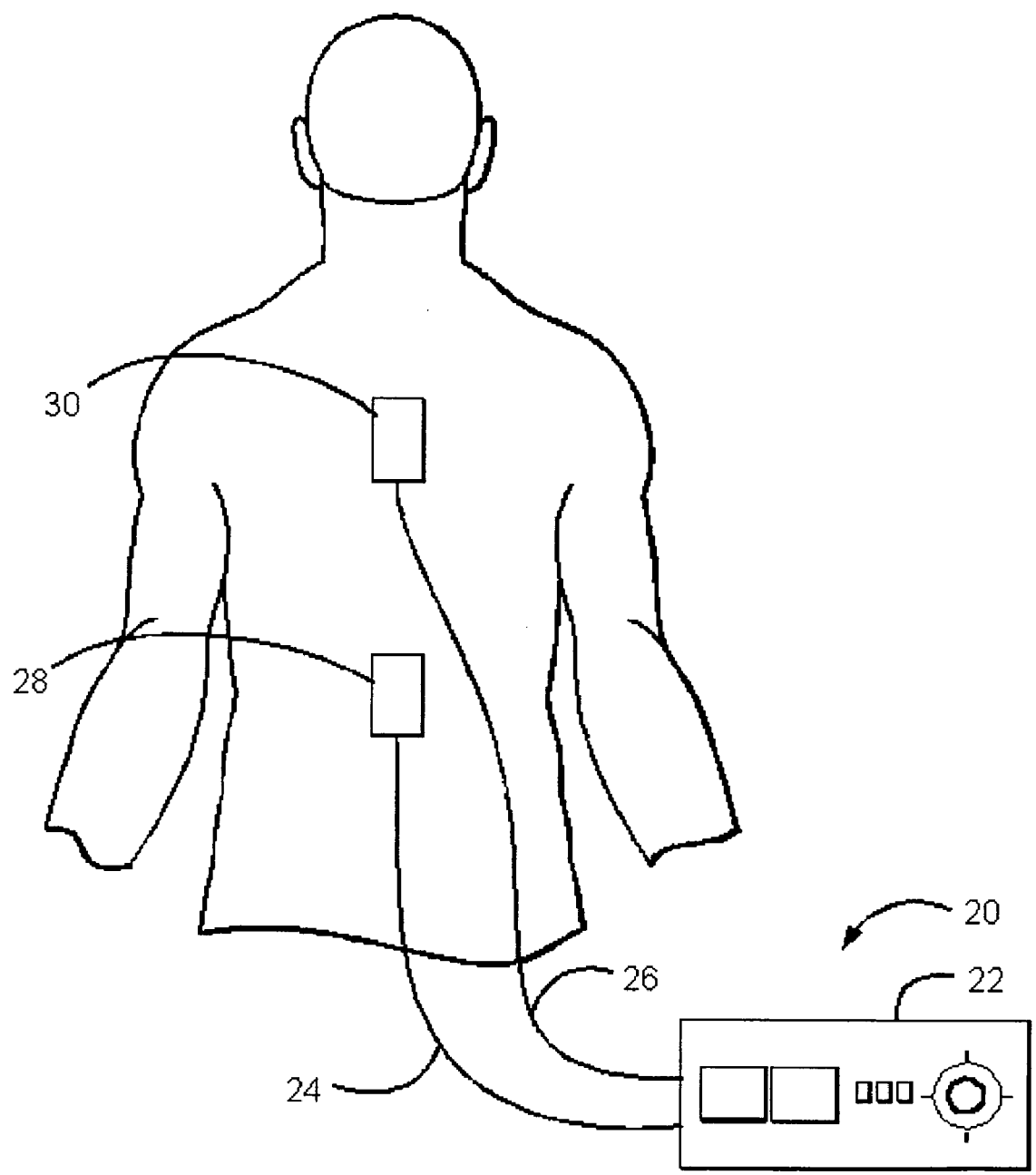
FIG. 1 is a rear view of a patient receiving the TENS treatment according to the present invention with the electrode pairs positioned vertically along the spinal column.

Referring now to FIG. 1, there is shown a patient receiving treatment according to the present invention via a TENS unit 20, including a stimulator 22, electrical leads 24, 26 and electrode pads 28,30 for affixation to the patient's skin. The TENS unit 20 for use in accordance with the present invention may be a conventional TENS device, such as the Isotron 1000 manufactured by XLTEK of Oakville, Ontario, Canada, or the INS PLUS device manufactured by BioMedical Life Systems of Vista, Calif. The stimulator 22 of the TENS unit 20 provides controllably variable parameters including current intensity, pulse frequency and pulse duration. Current intensity is the strength of the current applied, and may range from about 5 mA to about 100 mA in embodiments of the invention. The stimulator 22 delivers this current in pulses, and the rate of delivery of these pulses is the pulse frequency. In embodiments of the present invention, the pulse frequency may be variable from about 1 or 2 pulses per second (pps) up to about 300 pps.

Separate from the number of pulses per second, is the duration of each pulse, i.e., two separate treatment sessions may each apply pulses at a frequency of, for example, 5 pulses per second, but in the first session, each pulse may last 100 microseconds (μs) and in the second session each pulse may last 200 μs. In embodiments of the present invention, the pulse duration may vary between about 20 μs and 300 μs.

The pulses delivered by the stimulator 22 may be biphasic square wave pulses. The biphasic nature of the pulse generally prevents any net DC component, thus minimizing any skin reactions due to the build up of electrolytes under the electrodes. Each treatment session may last approximately a half hour to an hour, and may be conducted once a day.

It is understood that each of the above-described values for current intensity, pulse frequency, pulse duration, duration of each treatment session and the number of treatment sessions per day are by way of example only and should not be considered limiting on the invention. The values for current intensity, pulse frequency, pulse duration, duration of the treatment session and the number of treatment sessions per day may vary outside of the ranges set forth above in alternative embodiments.

The stimulator 22 may further offer a burst mode in which the stimulator emits a series of pulses and then a period of dormancy. For example, the stimulator 22 may emit 10 to 100 pulses in a second and be dormant for the next second. These numbers are by way of example and may vary in alternative embodiments. Moreover, a variable modulation mode may be provided in which the stimulator 22 successively varies one or more of the pulse frequency, pulse duration and bursts applied during a given treatment session.

The leads 24, 26 are conventional insulated electrical leads which are attached between the stimulator 22 and the electrode pads 28, 30. The electrode pads may conventionally be formed of a carbon silicone or metal mesh, and affix to the skin either by conductive adhesive, tape or gel. While a preferred embodiment of the present invention employs pads that are positioned on a patient's skin, it is understood that needles may be employed in alternative embodiments. As is known in the art of acupuncture, needles may be inserted subcutaneously and supplied an electric current as would the pads 28, 30 to electrically stimulate the nervous pathways innervating the stomach as described hereinafter.

The TENS unit 20 may further include a dual channel output in which two pairs of electrode pads can be stimulated simultaneously (not shown). Each set of electrode pads may have the same current intensity, pulse frequency and/or pulse duration, or the current intensity, pulse frequency and/or pulse duration may be different between the two sets of electrodes.

In preferred embodiments of the present invention, the electrode pads are situated proximate to the thoracic vertebrae and the preganglionic greater splanchnic nerve fibers of the spine to stimulate the postganglionic sympathetic nerve pathways innervating the stomach. In one embodiment of the present invention, as shown in FIG. 1, the electrode pads 28, 30 may be positioned at or near the top and bottom, respectively, of the thoracic spine. In particular, in one embodiment, the first electrode pad 28 may be positioned at thoracic vertebrae T1 and the second electrode pad 30 may be positioned at thoracic vertebrae T12. In a further embodiment, the first electrode pad 28 may be positioned at thoracic vertebrae T6 and the second electrode pad 30 may be positioned at thoracic vertebrae T10.

Figure 2:
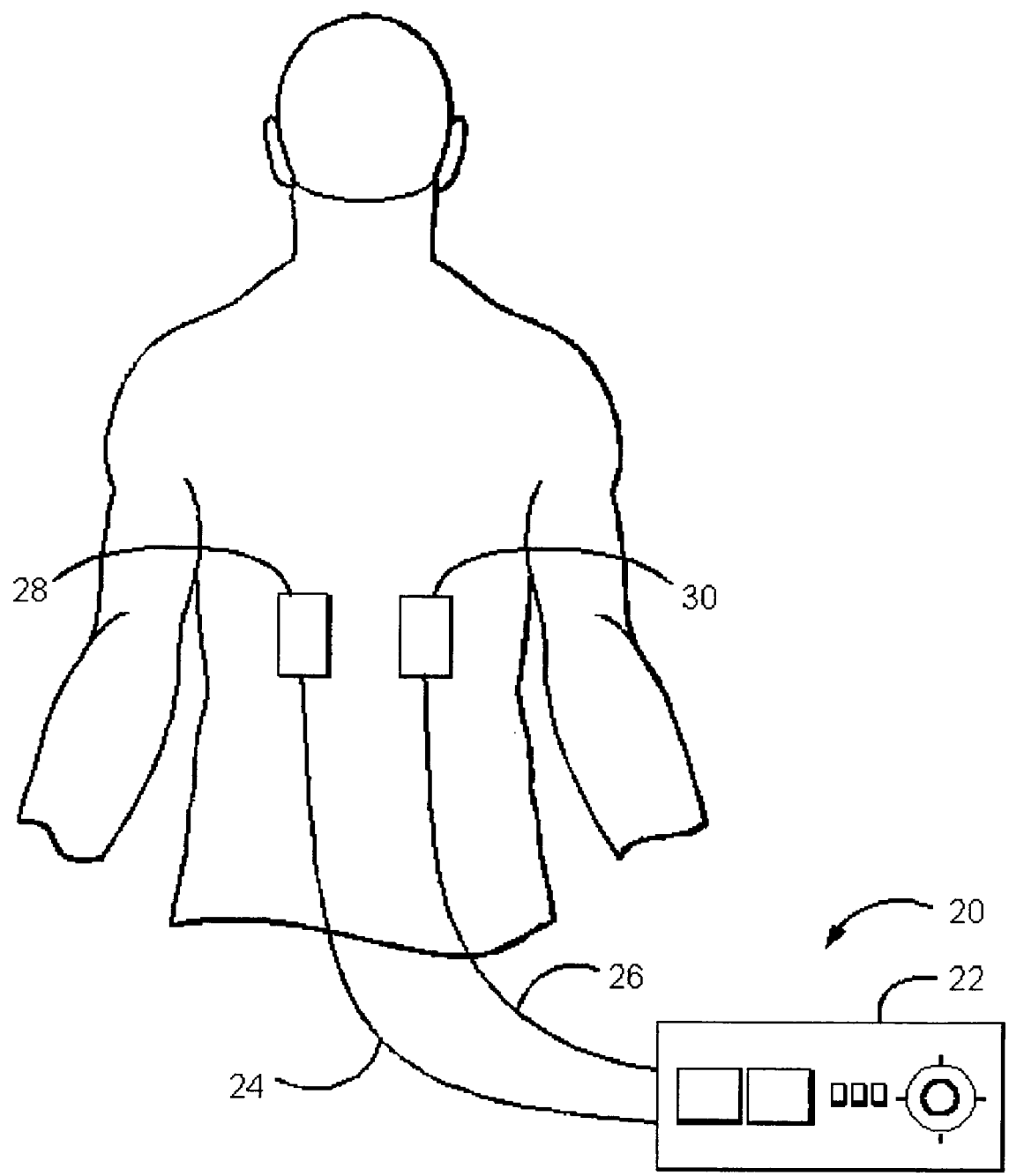
FIG. 2 is a rear view of a patient receiving the TENS treatment according to the present invention with the electrode pairs positioned horizontally on either side of the spinal column.

It is understood that the pads 28, 30 may be positioned at other locations in alternative embodiments. For example, the pads may be positioned at any two points along the spinal column (including the cervical, thoracic, lumbar and sacral spine). Moreover, as shown in FIG. 2, instead of a vertical orientation of the pads along the spine, the pads may have a horizontal orientation with respect to each other, on either side of a position along the spine. For example, according to the embodiment of FIG. 2, the pads 28, 30 may be positioned on either side of the thoracic vertebrae T1 through T12, and more particularly, on either side of vertebrae T6 through T10. The pads may be spaced approximately 1 inch to 4 inches horizontally from each other according to this embodiment, though the spacing may be greater or smaller than that in alternative embodiments.

Figure 3:
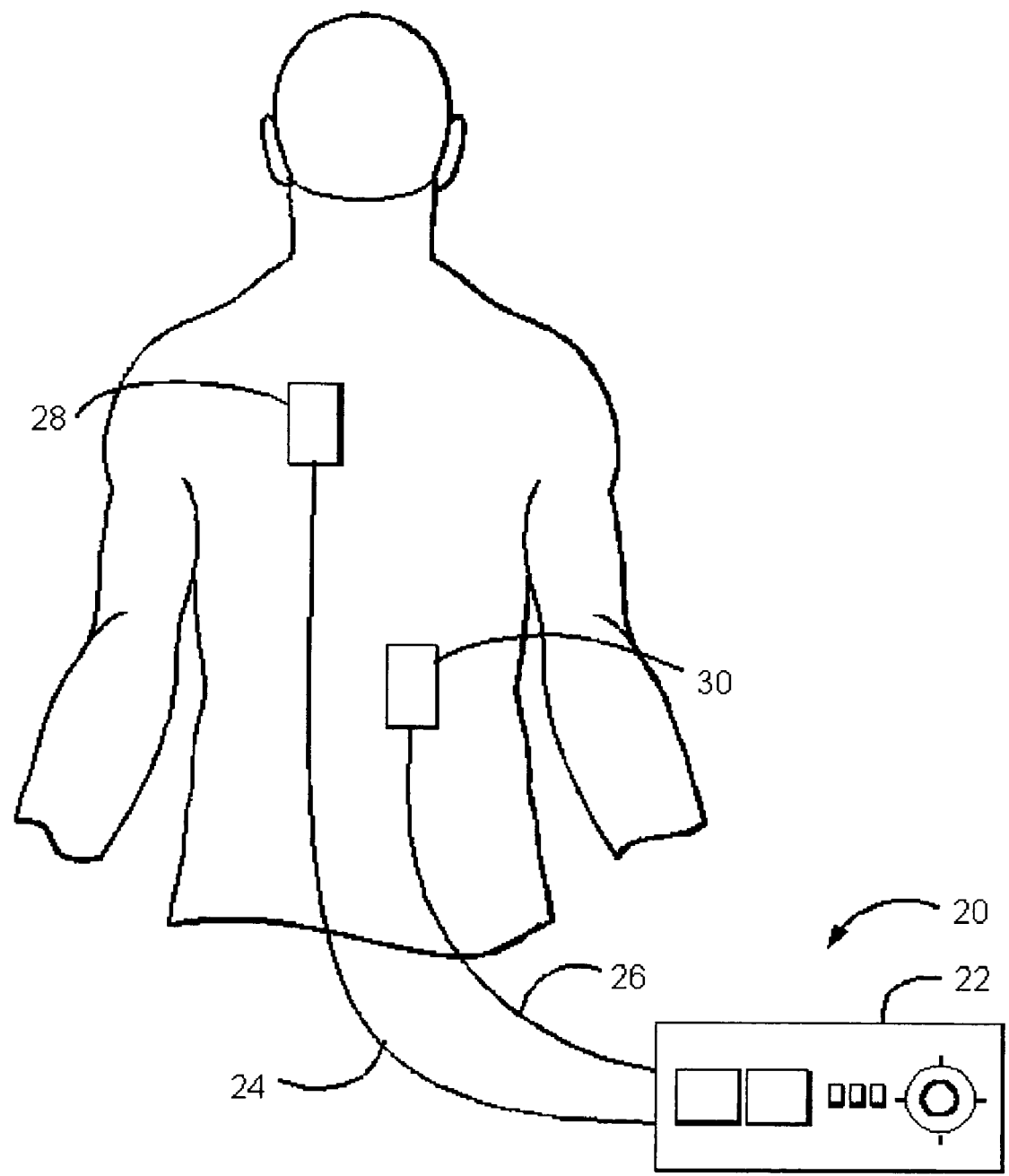
FIG. 3 is a rear view of a patient receiving the TENS treatment according to the present invention with the electrode pairs positioned diagonally with respect to each other on either side of the spinal column.

In a further alternative embodiment of the present invention shown in FIG. 3, the electrode pads may be space diagonally from each other with respect to the spine. The pads may be positioned vertically anywhere along the spinal column, for example horizontally aligned with the top and bottom of the thoracic spine. Alternatively, the pads may be horizontally aligned with T6 and T10 of the thoracic spine. The pads in this embodiment may be spaced approximately 1 inch to 4 inches horizontally from each other, evenly about the spine, though the spacing between the pads may be greater or smaller than that in alternative embodiments.

Figure 4:
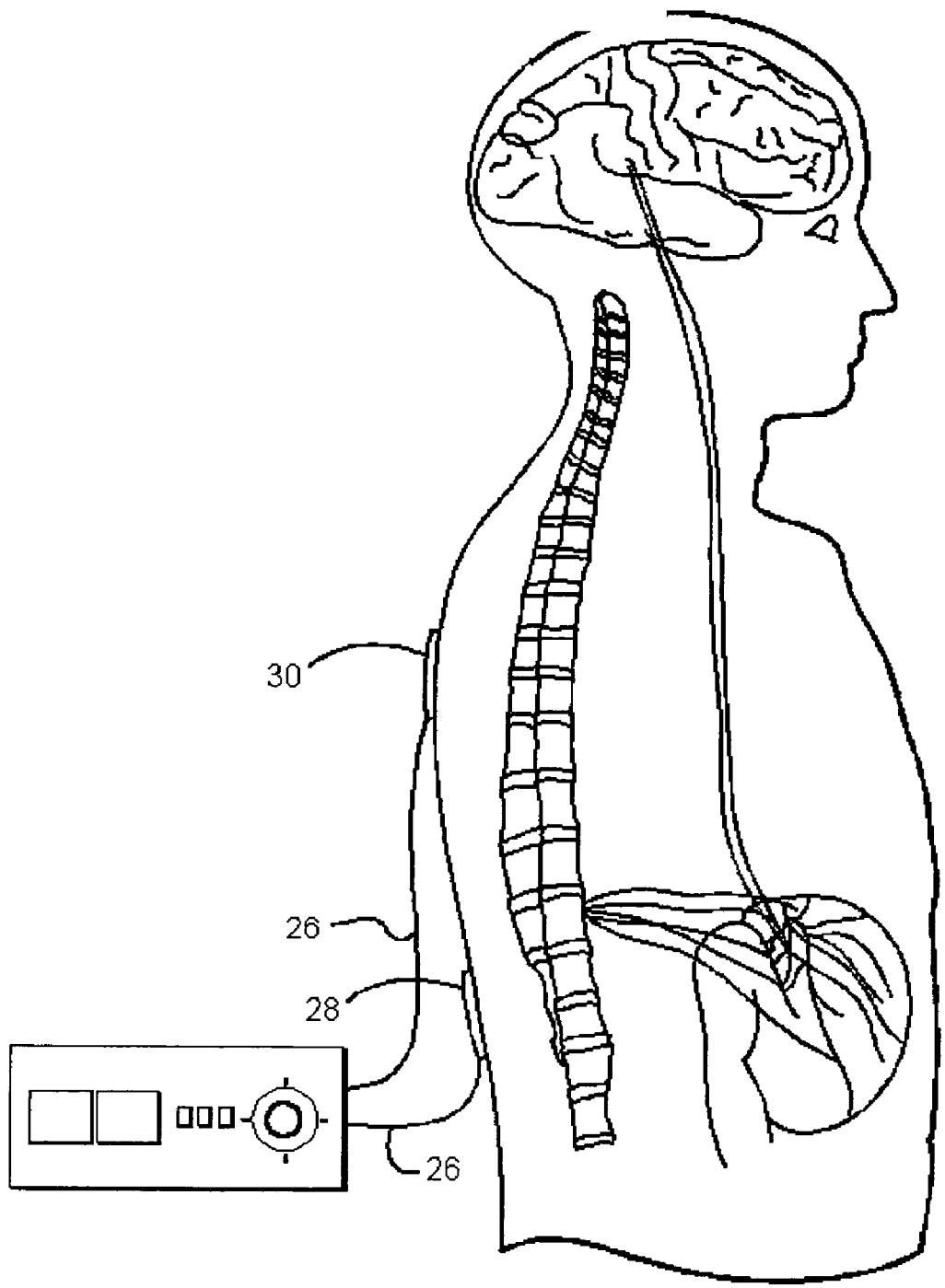
FIG. 4 is a side view of a patient's stomach and the nerves innervating the stomach.

Referring now to FIG. 4, the present invention operates by stimulating the nervous pathways innervating the stomach. It is believed the mechanism involves one or more of the following physiological processes. Applying TENS proximate the one or more thoracic vertebrae and the preganglionic greater splanchnic nerve fibers in accordance with the embodiments described above stimulates the sympathetic celiac ganglia. Stimulation of the celiac ganglia may interfere with or induce changes in the parasympathetic nerves responsible for gastric emptying and appetite. Additionally or alternatively, applying TENS proximate the spine or one or more thoracic vertebrae in accordance with the embodiments described above stimulates the celiac nerve plexus directly innervating the stomach. This may have one or more effects. First, it may generate nerve impulses to the brain which create the feeling of satiety, even if there little food in the stomach. Second, the nerve stimulation may suppress the activity of the gastric pacemaker and slow down peristalsis. Thus, the stomach fills up quickly and/or remains full so that normal nerve impulses are generated that create the feeling of satiety.

In operation, the pads 28 and 30 are positioned as described above and the current is applied. Initially during a treatment, the current intensity is low, and gradually turned up until the patient feels a tingling. There is unlikely to be a universal combination of current intensity, pulse frequency and pulse duration that will act to suppress appetite in all patients. Rather, the combination of current intensity, pulse frequency and pulse duration that works optimally will vary from patient to patient. The effect of varying the current intensity, pulse frequency and pulse duration will alter a user's bowel motility and symptoms, so that increases or reductions in appetite result. The optimal combination of current intensity, pulse frequency and pulse duration during the TENS treatment is therefore found for a given patient by varying one or more of these parameters over a number of treatments to see which combination creates the desired change in appetite or bowel motility. In particular, if a given combination of current intensity, pulse frequency, pulse duration does not result in appetite suppression, then at least one of current intensity, pulse frequency, pulse duration may be adjusted until the proper combination of parameters is found to result in appetite suppression.

After a TENS session is performed, the patient is monitored for gastric symptoms to see if any change occurred. In embodiments of the present invention, it is contemplated that a proper combination of current intensity, pulse frequency, pulse duration will result in appetite suppression after only a single session of TENS. In such embodiments, if appetite suppression does not occur after a single session, one or more of the parameters may be changed in succeeding sessions until the proper combination is identified.

In still further embodiments of the present invention, it is contemplated that a proper combination of current intensity, pulse frequency, pulse duration will not result in appetite suppression after a single session of TENS, but rather only after multiple sessions. In such embodiments, if appetite suppression does not occur after multiple sessions, then one or more of the parameters may be changed and the process repeated until the proper combination is identified. In this embodiment, it is contemplated that if no suppression of appetite occurs after 2 to 10 sessions, then one or more of the parameters would be changed and the process repeated. In further embodiments, if no suppression of appetite occurs after 3 to 5 sessions, then one or more of the parameters would be changed and the process repeated. It is understood that the number of sessions before a parameter is changed may be greater than 10 and other than the number of sessions set forth above in alternative embodiments.

It is also conceivable that the combination of current intensity, pulse frequency and pulse duration, once found, may change over time. In this instance, the parameters may be varied to once again identify the optimal combination for appetite suppression.

As described above, it is an advantage of the present invention to perform TENS to stimulate the sympathetic nervous pathways innervating the stomach to suppress appetite. It is a further advantage of the present invention to deliberately hypersensitive the sympathetic nervous pathways innervating the stomach so that, over time, a given TENS treatment will generate a faster and more pronounced response to the stimulus. This occurs with repeated stimulation of the sympathetic nervous pathways with the TENS procedure described above. The exact time it takes to generate this hypersensitivity may vary from patient to patient, but it may occur for example anywhere from 5 to 20 days after the procedures begin.

Up to this point, the present invention has been described as stimulating the sympathetic nervous pathways from the spine. However, in an alternative embodiment, TENS stimulation of the sympathetic nervous pathways may also be combined with TENS stimulation of the parasympathetic nervous pathways to inhibit gastric emptying, suppress appetite and create the impression of satiety. According to this embodiment, a dual channel stimulator 22 as described above may be used so that a first pair of electrode pads may be positioned proximate the thoracic spine as described above, and the second pair of electrode pads may be positioned to stimulate the vagus nerve pathways from the brain. In this embodiment, the first pair of electrode pads may be positioned as indicated above, and the second pair of electrodes may be positioned at or near the neck area, adjacent the vagus nerves.

While a preferred embodiment of the present invention acts to suppress appetite, in alternative embodiments, the present invention may be used to increase appetite. This embodiment may be used to treat conditions of severe weight loss and abnormal loss of appetite, such as occurs for example with anorexia nervosa. In this embodiment, stimulation of the celiac ganglia as described above may induce changes in the parasympathetic nerves responsible for gastric emptying and appetite. Additionally or alternatively, applying TENS proximate the spine or one or more thoracic vertebrae in accordance with the embodiments described above stimulates the celiac nerve plexus directly innervating the stomach. This may have one or more effects. First, it may generate nerve impulses to the brain which create the feeling of hunger. Second, the nerve stimulation may increase the activity of the gastric pacemaker and speed up peristalsis. Thus, the stomach empties quickly so that normal nerve impulses are generated that create the feeling of hunger.

For a given patient, the combination of current intensity, pulse frequency and pulse duration that induce greater appetite is of course different than the combination of current intensity, pulse frequency and pulse duration that would induce appetite suppression. While the combination to bring about the desired result will vary in each patient, in general, greater stimulation for longer periods of time will slow down the activity of the gut to decrease and suppress appetite. If the desired effect is appetite suppression therefore, longer stimulation periods at higher current intensity, pulse frequency and/or pulse duration will tend to bring about this effect. Conversely, if the desired effect is greater appetite, shorter stimulation periods at lower current intensity, pulse frequency and/or pulse duration will tend to bring about this effect. Within these parameters, in each patient, combinations of current intensity, pulse frequency and pulse duration are tested and varied as necessary until the proper combination is found that brings about the desired effect, i.e., increased appetite or appetite suppression. It is further conceivable that a given combination of current intensity, pulse frequency and pulse duration will induce greater appetite in one patient, while the same combination of current intensity, pulse frequency and pulse duration will suppress appetite in another patient.

It is further understood that the present invention may also be used to treat gastroparesis in alternative embodiments. Gastroparesis involves a slowing or stopping of the natural gastric slow wave pacemaker activity of the stomach. This activity is controlled by the enteric nerve plexus. As indicated above, stimulation of the sympathetic celiac nerve fibers in accordance with the present invention may effectively stimulate enteric nerve plexus to facilitate normal gastric pacing. As with using TENS according to the present invention to reduce appetite, the use of TENS according to the present invention to facilitate gastric pacing may be accomplished for a given patient by varying current intensity, pulse frequency and/or pulse duration during the TENS treatment over a number of treatments to see which combination facilitates gastric pacing.

EXAMPLE

In one patient, TENS was applied once a day for a period of 21 days for severe gastroparesis, loss of appetite, and weight loss (prior to treatment, patient went from 70 kg to 62 kg body weight). TENS was applied using the Isotron 1000 (from XLTEK) for 30 minutes daily over 21 days. Within 2 days of starting TENS his gastric symptoms resolved. Within a week he was able to tolerate a normal diet without symptoms and he discontinued pro-motility medication. Within 6 months, he had no gastrointestinal complaints, he had regained a normal appetite and diet, without the use of any pro-motility medication, and he gained 8 kg in body weight to return to his normal weight. In this case the machine was used to stimulate appetite and relieve the symptoms of early satiety. The machine stimulated electrodes that were placed over the spine (one in the neck at C7, one on the sacrum). The voltages that were used were: six minutes at 15 milliamps and then six minutes at 30 milliamps, at a range of 150–180 pulses per minute (ppm) with a continuous sine wave of stimulation.

In further embodiments of the present invention, TENS as described above may be used to treat other abnormalities of bowel motility. These abnormalities include dumping syndrome, irritable bowel syndrome, spastic colon, constipation, and disorders of rapid bowel transit. As above, each of these conditions may be treated by TENS by varying the combination of current intensity, pulse frequency and pulse duration until the proper combination is found to bring about the desired effect.

Although the invention has been described in detail herein, it should be understood that the invention is not limited to the embodiments herein disclosed. Various changes, substitutions and modifications may be made to the disclosure by those skilled in the art without departing from the spirit or scope of the invention as described and defined by the appended claims.

I claim:

1. A method of suppressing appetite in an individual, comprising the steps of:
   (a) applying an electrical current to the skin of the individual in at least one session to stimulate the nerve pathways innervating the stomach, the current having a current intensity, pulse frequency and pulse duration;
   (b) monitoring the effect of the current applied in said step (a) on the individual's appetite; and
   (c) adjusting at least one of the current intensity, pulse frequency, pulse duration if said step (b) indicates that said step (a) does not suppress the individual's appetite, wherein said step (a) of applying an electrical current to the skin of the individual comprises the steps of locating a first electrode approximately at a top of the spine and a second electrode at approximately a bottom of the spine.

2. A method of suppressing appetite in an individual, comprising the steps of:

(a) applying an electrical current to the skin of the individual in at least one session to stimulate the nerve pathways innervating the stomach, the current having a current intensity, pulse frequency and pulse duration;
(b) monitoring the effect of the current applied in said step (a) on the individual's appetite; and
(c) adjusting at least one of the current intensity, pulse frequency, pulse duration if said step (b) indicates that said step (a) does not suppress the individual's appetite, wherein said step (a) of applying an electrical current to the skin of the individual comprises the steps of locating a first electrode approximately at a top of the thoracic spine and a second electrode at approximately a bottom of the thoracic spine.

3. A method of suppressing appetite in an individual, comprising the steps of:
(a) applying an electrical current to the skin of the individual in at least one session to stimulate the nerve pathways innervating the stomach, the current having a current intensity, pulse frequency and pulse duration;
(b) monitoring the effect of the current applied in said step (a) on the individual's appetite; and
(c) adjusting at least one of the current intensity, pulse frequency, pulse duration if said step (b) indicates that said step (a) does not suppress the individual's appetite, wherein said step (a) of applying an electrical current to the skin of the individual comprises the steps of locating a first electrode approximately at T6 of the thoracic spine and a second electrode at approximately T10 of the thoracic spine.

4. A method of suppressing appetite in an individual, comprising the steps of:
(a) applying an electrical current to the skin of the individual in at least one session to stimulate the nerve pathways innervating the stomach, the current having a current intensity, pulse frequency and pulse duration;
(b) monitoring the effect of the current applied in said step (a) on the individual's appetite; and
(c) adjusting at least one of the current intensity, pulse frequency, pulse duration if said step (b) indicates that said step (a) does not suppress the individual's appetite, wherein said step (a) of applying an electrical current to the skin of the individual comprises the steps of locating a first electrode to the left of, and a second electrode to the right of, one of T6 through T10 of the thoracic spine.

5. A method of suppressing appetite in an individual, comprising the steps of:
(a) applying an electrical current to the skin of the individual in at least one session to stimulate the nerve pathways innervating the stomach, the current having a current intensity, pulse frequency and pulse duration;
(b) monitoring the effect of the current applied in said step (a) on the individual's appetite; and
(c) adjusting at least one of the current intensity, pulse frequency, pulse duration if said step (b) indicates that said step (a) does not suppress the individual's appetite, wherein said step (a) of applying an electrical current to the skin of the individual comprises the steps of locating a first electrode to the left of a first portion of the spine, and a second electrode to the right of a second portion of the spine below the first portion.

6. A method of suppressing appetite in an individual, comprising the step of:

(a) applying transcutaneous electrical nerve stimulation with a first electrode at a first point on the skin proximate the individual's spine and with a second electrode at a second point on the skin proximate the individual's spine in at least one session to stimulate the sympathetic celiac ganglia, the stimulation of the sympathetic celiac ganglia resulting in appetite suppression further comprising a step of adjusting one or more of the parameters of the electrical current of the transcutaneous electrical nerve stimulation to optimize the current for appetite suppression.

7. A method of a treating gastrointestinal disorder in an individual, comprising the steps of:
(a) applying transcutaneous electrical nerve stimulation with a first electrode at a first point on the skin proximate the individual's spine and with a second electrode at a second point on the skin proximate the individual's spine in at least one session to stimulate the sympathetic celiac ganglia;
(b) monitoring the effect of the transcutaneous electrical nerve stimulation in said step (a) on the individual's gastrointestinal disorder; and
(c) adjusting parameters of the transcutaneous electrical nerve stimulation if said step (b) indicates that said step (a) does not improve the condition of the gastrointestinal disorder.

8. A method of a treating gastrointestinal disorder in an individual as recited in claim 7, wherein the gastrointestinal disorder is obesity.

9. A method of a treating gastrointestinal disorder in an individual as recited in claim 7, wherein the gastrointestinal disorder is gastroparesis.

10. A method of a treating gastrointestinal disorder in an individual as recited in claim 7, wherein the gastrointestinal disorder is severe weight loss or abnormal loss of appetite.

11. A method of a treating gastrointestinal disorder in an individual as recited in claim 7, wherein the gastrointestinal disorder dumping syndrome.

12. A method of a treating gastrointestinal disorder in an individual as recited in claim 7, wherein the gastrointestinal disorder is irritable bowel syndrome.

13. A method of a treating gastrointestinal disorder in an individual as recited in claim 7, wherein the gastrointestinal disorder is spastic colon.

14. A method of a treating gastrointestinal disorder in an individual as recited in claim 7, wherein the gastrointestinal disorder is constipation.

15. A method of a treating gastrointestinal disorder in an individual as recited in claim 7, wherein the gastrointestinal disorder are disorders of rapid bowel transit.

16. A method of a treating gastrointestinal disorder in an individual as recited in claim 7, wherein said step (a) of applying an electrical current to the skin of the individual comprises the steps of locating a first electrode approximately at T6 of the thoracic spine and a second electrode at approximately T10 of the thoracic spine.

17. A method of a treating gastrointestinal disorder in an individual as recited in claim 7, wherein said step (a) of applying an electrical current to the skin of the individual comprises the steps of locating a first electrode to the left of, and a second electrode to the right of, one of T6 through T10 of the thoracic spine.

* * * * *